(12) United States Patent
Rehman

(10) Patent No.: US 10,551,172 B2
(45) Date of Patent: Feb. 4, 2020

(54) METROLOGY METHOD, APPARATUS AND COMPUTER PROGRAM

(71) Applicant: ASML NETHERLANDS B.V., Veldhoven (NL)

(72) Inventor: Samee Ur Rehman, Eindhoven (NL)

(73) Assignee: ASML Netherlands B.V., Veldhoven (NL)

( * ) Notice: Subject to any disclaimer, the term of this patent is extended or adjusted under 35 U.S.C. 154(b) by 92 days.

(21) Appl. No.: 15/873,880

(22) Filed: Jan. 17, 2018

(65) Prior Publication Data

US 2018/0216930 A1 Aug. 2, 2018

(30) Foreign Application Priority Data

Feb. 2, 2017 (EP) .................................. 17154425

(51) Int. Cl.
*G01B 11/24* (2006.01)
*G03F 7/20* (2006.01)
(Continued)

(52) U.S. Cl.
CPC .............. *G01B 11/24* (2013.01); *G01B 11/30* (2013.01); *G03F 7/70625* (2013.01);
(Continued)

(58) Field of Classification Search
CPC ..... G01B 11/24; G01B 11/30; G03F 7/70625; G03F 7/7065; G03F 7/70633; G01N 21/95607
(Continued)

(56) References Cited

U.S. PATENT DOCUMENTS 7,061,615 B1    6/2006 Lowe-Webb
7,373,216 B1 *  5/2008 Winkler et al. .. G05B 19/41875
                                                        700/121
(Continued)

FOREIGN PATENT DOCUMENTS

WO    2009/078708    6/2009
WO    2009/106279    9/2009
(Continued)

OTHER PUBLICATIONS

Notification of Transmittal of the International Search Report and the Written Opinion of the International Searching Authority dated Apr. 13, 2018, in corresponding International Patent Application No. PCT/EP2018/050366.
(Continued)

*Primary Examiner* — Sun J Lin
(74) *Attorney, Agent, or Firm* — Pillsbury Winthrop Shaw Pittman LLP

(57) ABSTRACT

Disclosed herein is a metrology method, and an associated metrology apparatus, the metrology method includes measuring a target formed in at least two layers on a substrate by a lithographic process and capturing at least one corresponding pair of non-zeroth diffraction orders, for example in an image field, to obtain measurement data. A simulation of a measurement of the target as defined in terms of geometric parameters of the target, the geometric parameters including one or more variable geometric parameters, is performed and a difference between the measurement data and simulation data is minimized, so as to directly reconstruct a value for each of the one or more variable geometric parameters.

20 Claims, 6 Drawing Sheets

(51) Int. Cl.
*G01B 11/30* (2006.01)
*G01N 21/956* (2006.01)

(52) U.S. Cl.
CPC ... *G03F 7/70633* (2013.01); *G01N 21/95607* (2013.01); *G03F 7/7065* (2013.01)

(58) Field of Classification Search
USPC ..................................................... 716/51, 54
See application file for complete search history.

(56) References Cited

U.S. PATENT DOCUMENTS

| | | | | |
|---|---|---|---|---|
| 7,580,823 | B2* | 8/2009 | Jakatdar et al. | G06F 17/5009 703/13 |
| 7,587,704 | B2* | 9/2009 | Ye et al. | G03F 7/70441 378/35 |
| 8,024,676 | B2* | 9/2011 | Carcasi et al. | G03F 7/70625 378/35 |
| 8,078,995 | B2* | 12/2011 | Tirapu Azpiroz | G03F 1/36 430/5 |
| 8,411,287 | B2 | 4/2013 | Smilde et al. | |
| 8,867,020 | B2 | 10/2014 | Smilde et al. | |
| 9,081,303 | B2 | 7/2015 | Cramer et al. | |
| 2003/0163295 | A1* | 8/2003 | Jakatdar et al. | G06F 17/5009 703/14 |
| 2007/0061773 | A1* | 3/2007 | Ye et al. | G03F 7/70441 716/52 |
| 2011/0027704 | A1 | 2/2011 | Cramer et al. | |
| 2011/0043791 | A1 | 2/2011 | Smilde et al. | |
| 2011/0080585 | A1 | 4/2011 | Rabello et al. | |
| 2012/0242970 | A1 | 9/2012 | Smilde et al. | |
| 2015/0043803 | A1 | 2/2015 | Jeong | |
| 2015/0186582 | A1 | 7/2015 | Chen et al. | |
| 2016/0161863 | A1 | 6/2016 | Den Boef et al. | |
| 2016/0161864 | A1* | 6/2016 | Middlebrooks et al. | G03F 7/70633 355/67 |
| 2016/0334326 | A1* | 11/2016 | Sapiens et al. | G03F 7/70625 |
| 2017/0023491 | A1* | 1/2017 | Cao et al. | G01N 21/211 |
| 2018/0292761 | A1* | 10/2018 | Cekli et al. | G03F 7/70258 |

FOREIGN PATENT DOCUMENTS

| | | |
|---|---|---|
| WO | 2011/012624 | 2/2011 |
| WO | 2016/083076 | 6/2016 |

OTHER PUBLICATIONS

Adam Urbanczyk et al., U.S. Appl. No. 62/453,743, filed Feb. 2, 2017.
Extended European Search Report dated Dec. 11, 2017 in corresponding European Application No. 17154425.7.

* cited by examiner

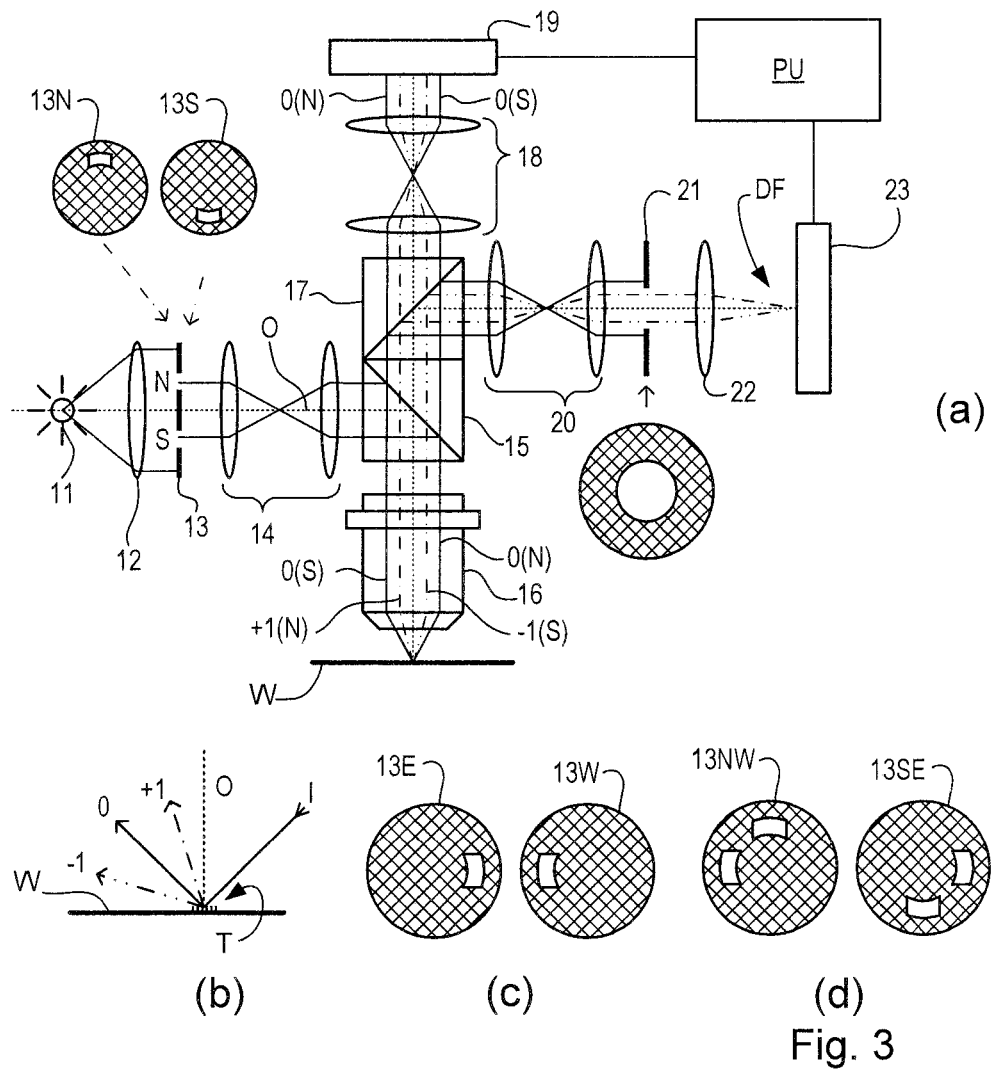
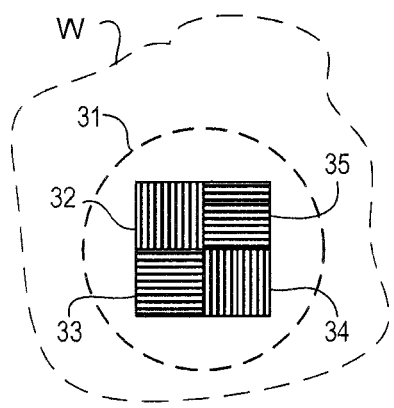
Fig. 4
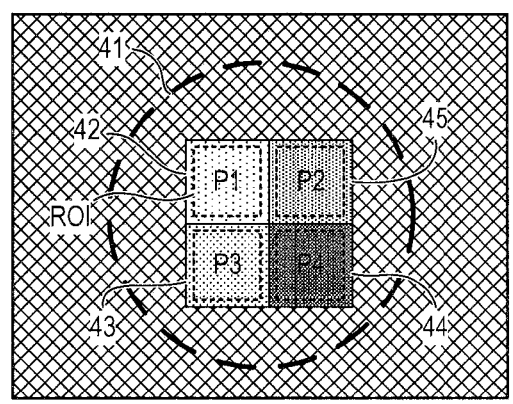
Fig. 5

METROLOGY METHOD, APPARATUS AND COMPUTER PROGRAM

This application claims priority to European patent application no. EP17154425, filed Feb. 2, 2017, which is incorporated herein in its entirety by reference.

FIELD

The present description relates to a method, apparatus, and computer product for metrology usable, for example, in the manufacture of devices by a lithographic technique and to a method of manufacturing devices using a lithographic technique.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned.

In a lithographic process (i.e., a process of developing a device or other structure involving lithographic exposure, which may typically include one or more associated processing steps such as development of resist, etching, etc.), it is desirable frequently to make measurements of structures created, e.g., for process control and verification. Various tools for making such measurements are known, including scanning electron microscopes, which are often used to measure critical dimension (CD), and specialized tools to measure overlay, the accuracy of alignment of two layers of a substrate. Recently, various forms of scatterometers have been developed for use in the lithographic field. These devices direct a beam of radiation onto a target and Measure one or more properties of the scattered radiation—e.g., intensity at a single angle of reflection as a function of wavelength; intensity at one or more wavelengths as a function of reflected angle; or polarization as a function of reflected angle—to obtain a "spectrum" from which a property of interest of the target can be determined. Determination of the property of interest may be performed by various techniques: e.g., reconstruction of the target structure by iterative approaches such as rigorous coupled wave analysis or finite element methods; library searches; and principal component analysis.

SUMMARY

Metrology apparatuses are sensitive to target structural asymmetry caused by, for example, a processing step such as etching, chemical mechanical polishing (CMP), deposition, etc. Such asymmetry leads to a measurement error that can be of the order of a few nanometers. This effect may start to dominate the overlay budget and solutions are therefore desired.

Asymmetry in the shape of a periodic structure of a target will generally have an impact on the measured overlay. This impact can vary depending on the illumination setting used for the measurement.

Other parameters which should be monitored include the heights of some or all of the layers within a stack. Measurement of layer heights is usually performed on dedicated thin film targets, separate to overlay and alignment targets. These take up additional substrate area, and their measurement takes additional measurement time.

It is desirable to provide a method and apparatus for (e.g., overlay) metrology using a target, in which throughput, flexibility and/or accuracy can be improved. Furthermore, although embodiments of the invention are not limited to this, it would be of advantage if this could be applied to small target structures that can be read out with a dark-field technique.

In an aspect, there is provided a metrology method comprising: obtaining measurement data relating to a measurement of a target formed in at least two layers on a substrate by a lithographic process, the measurement data being derived from at least one corresponding pair of non-zeroth diffraction orders; obtaining simulation data relating to simulation of a measurement of the target as defined in terms of geometric parameters of the target, the geometric parameters comprising one or more variable geometric parameters; and minimizing the difference between the measurement data and simulation data, so as to directly reconstruct values for the one or more variable geometric parameters.

In an aspect, there is provided a metrology apparatus comprising a processor operable to at least: obtain measurement data relating to a measurement of a target formed in at least two layers on a substrate by a lithographic process, the measurement data being derived from at least one corresponding pair of non-zeroth diffraction orders; obtain simulation data relating to simulation of a measurement of the target as defined in terms of geometric parameters of the target, the geometric parameters comprising one or more variable geometric parameters; and minimize the difference between the measurement data and simulation data, so as to directly reconstruct values for the one or more variable geometric parameters.

In aspect, there is provided a computer program and associated computer program carrier configured to carry out a method as described herein.

BRIEF DESCRIPTION OF THE DRAWINGS

Embodiments of the invention will now be described, by way of example only, with reference to the accompanying drawings in which.

FIG. 3A is schematic diagram of a measurement apparatus for use in measuring targets using a first pair of illumination apertures providing certain illumination modes;

FIG. 3B is a schematic detail of a diffraction spectrum of a target for a given direction of illumination;

FIG. 3C is a schematic illustration of a second pair of illumination apertures providing further illumination modes in using a measurement apparatus for diffraction based measurements;

FIG. 3D is a schematic illustration of a third pair of illumination apertures combining the first and second pairs of apertures providing further illumination modes in using a measurement apparatus for diffraction based measurements;

FIG. 4 depicts a form of multiple periodic structure (e.g., multiple grating) target and an outline of a measurement spot on a substrate;

FIG. 5 depicts an image of the target of FIG. 4 obtained in the apparatus of FIG. 3;

DETAILED DESCRIPTION

Before describing embodiments in detail, it is instructive to present an example environment in which embodiments may be implemented.

Figure 1:
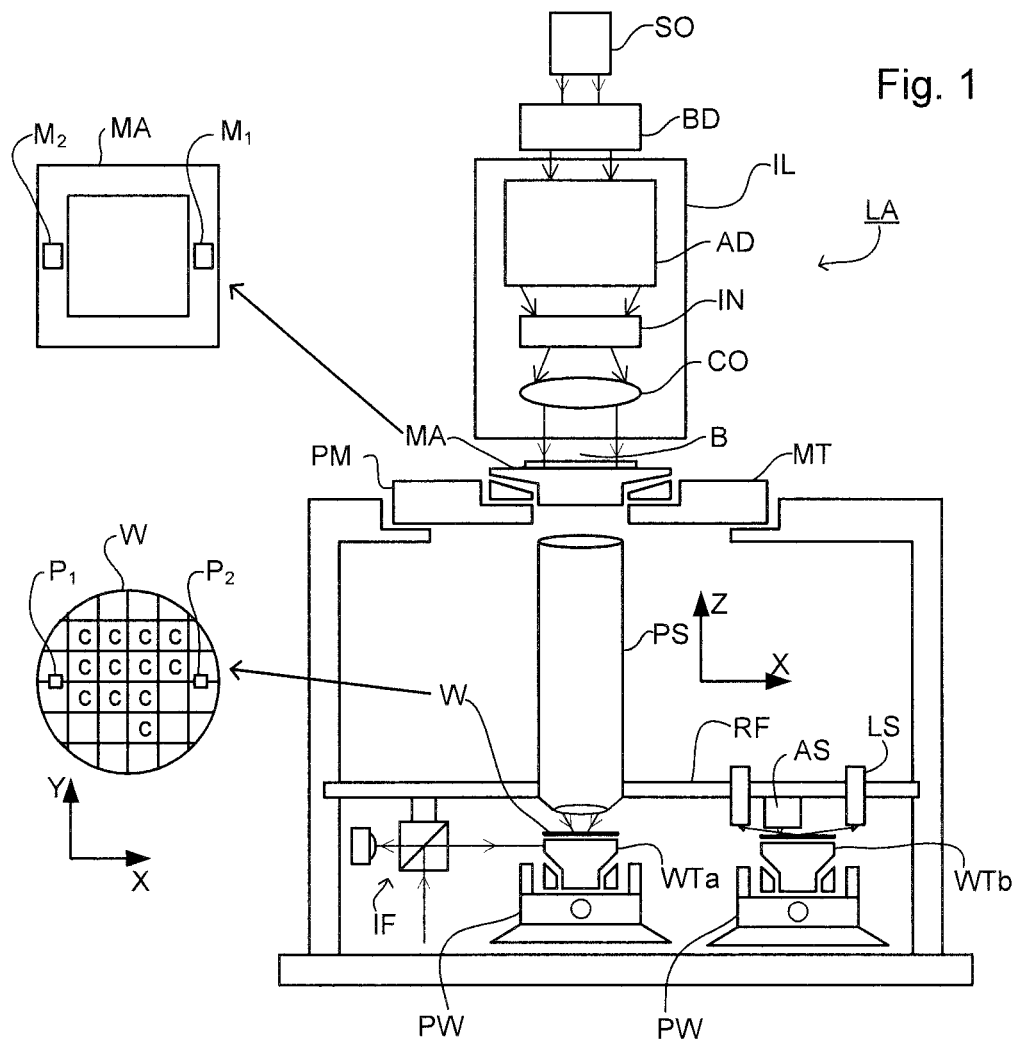
FIG. 1 depicts a lithographic apparatus according to an embodiment.

FIG. 1 schematically depicts a lithographic apparatus LA. The apparatus includes an illumination system (illuminator) IL configured to condition a radiation beam B (e.g., UV radiation or DUV radiation), a patterning device support or support structure (e.g., a mask table) MT constructed to support a patterning device (e.g., a mask) MA and connected to a first positioner PM configured to accurately position the patterning device in accordance with certain parameters; a substrate table (e.g., a wafer table) WT constructed to hold a substrate (e.g., a resist coated wafer) W and connected to a second positioner PW configured to accurately position the substrate in accordance with certain parameters; and a projection system (e.g., a refractive projection lens system) PS configured to project a pattern imparted to the radiation beam B by patterning device MA onto a target portion C (e.g., including one or more dies) of the substrate W.

The illumination system may include various types of optical components, such as refractive, reflective, magnetic, electromagnetic, electrostatic or other types of optical components, or any combination thereof, for directing, shaping, or controlling radiation.

The patterning device support holds the patterning device in a manner that depends on the orientation of the patterning device, the design of the lithographic apparatus, and other conditions, such as for example whether or not the patterning device is held in a vacuum environment. The patterning device support can use mechanical, vacuum, electrostatic or other clamping techniques to hold the patterning device. The patterning device support may be a frame or a table, for example, which may be fixed or movable as required. The patterning device support may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

As here depicted, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may include an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may include various other components, such as an integrator IN and a condenser CO. The illuminator may be used to condition the radiation beam, to have a desired uniformity and intensity distribution in its cross section.

The radiation beam B is incident on the patterning device (e.g., mask) MA, which is held on the patterning device support (e.g., mask table MT), and is patterned by the patterning device. Having traversed the patterning device (e.g., mask) MA, the radiation beam B passes through the projection system PS, which focuses the beam onto a target portion C of the substrate W. With the aid of the second positioner PW and position sensor IF (e.g., an interferometric device, linear encoder, 2-D encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the patterning device (e.g., mask) MA with respect to the path of the radiation beam B, e.g., after mechanical retrieval from a mask library, or during a scan.

Patterning device (e.g., mask) MA and substrate W may be aligned using mask alignment marks $M_1$, $M_2$ and substrate alignment marks $P_1$, $P_2$. Although the substrate alignment marks as illustrated occupy dedicated target portions, they may be located in spaces between target portions (these are known as scribe-lane alignment marks). Similarly, in situations in which more than one die is provided on the patterning device (e.g., mask) MA, the mask alignment marks may be located between the dies. Small alignment markers may also be included within dies, in amongst the device features, in which case it is desirable that the markers be as small as possible and not require any different imaging or process conditions than adjacent features. An embodiment of an alignment system, which can detect the alignment markers, is described further below.

The depicted apparatus could be used in at least one of the following modes:

1. In step mode, the patterning device support (e.g., mask table) MT and the substrate table WTa are kept essentially stationary, while an entire pattern imparted to the radiation beam is projected onto a target portion C at one time (i.e., a single static exposure). The substrate table WTa is then shifted in the X and/or Y direction so that a different target portion C can be exposed. In step mode, the maximum size of the exposure field limits the size of the target portion C imaged in a single static exposure.

2. In scan mode, the patterning device support (e.g., mask table) MT and the substrate table WTa are scanned synchronously while a pattern imparted to the radiation beam is projected onto a target portion C (i.e., a single dynamic exposure). The velocity and direction of the substrate table WTa relative to the patterning device support (e.g., mask table) MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In another mode, the patterning device support (e.g., mask table) MT is kept essentially stationary holding a programmable patterning device, and the substrate table WTa is moved or scanned while a pattern imparted to the radiation beam is projected onto a target portion C. In this mode, generally a pulsed radiation source is employed and the programmable patterning device is updated as required after each movement of the substrate table WTa or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Lithographic apparatus LA is of a so-called dual stage type which has two tables WTa, WTb (e.g., two substrate tables) and two stations—an exposure station and a measurement station—between which the tables can be exchanged. For example, while a substrate on one table is being exposed at the exposure station, another substrate can be loaded onto the other substrate table at the measurement station and various preparatory steps carried out. The preparatory steps may include mapping the surface control of the substrate using a level sensor LS and measuring the position of alignment markers on the substrate using an alignment sensor AS, both sensors being supported by a reference frame RF. If the position sensor IF is not capable of measuring the position of a table while it is at the measurement station as well as at the exposure station, a second position sensor may be provided to enable the positions of the table to be tracked at both stations. As another example, while a substrate on one table is being exposed at the exposure station, another table without a substrate waits at the measurement station (where optionally measurement activity may occur). This other table has one or more measurement devices and may optionally have other tools (e.g., cleaning apparatus). When the substrate has completed exposure, the table without a substrate moves to the exposure station to perform, e.g., measurements and the table with the substrate moves to a location (e.g., the measurement station) where the substrate is unloaded and another substrate is load. These multi-table arrangements enable a substantial increase in the throughput of the apparatus.

Figure 2:
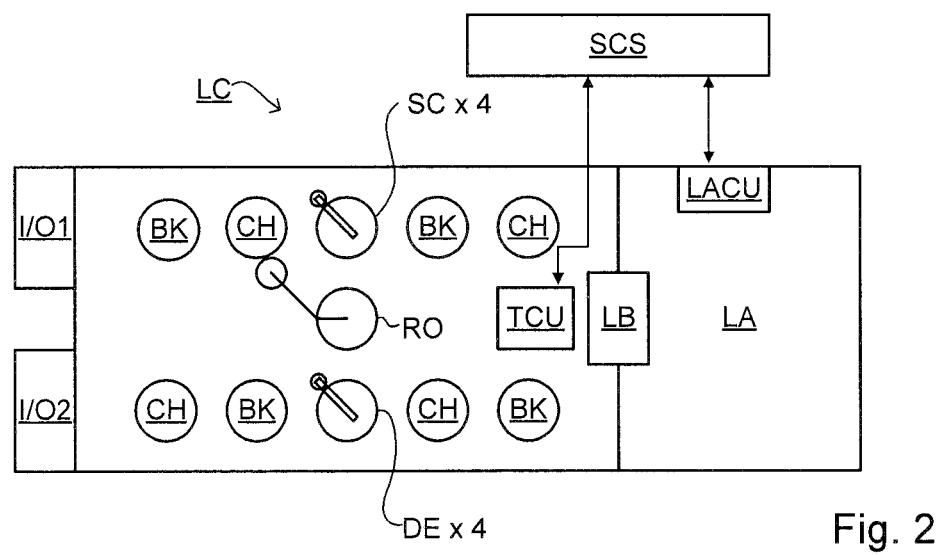
FIG. 2 depicts a lithographic cell or cluster according to an embodiment.

As shown in FIG. 2, the lithographic apparatus LA forms part of a lithographic cell LC, also sometimes referred to as a lithocell or lithocluster, which also includes apparatus to perform one or more pre- and post-exposure processes on a substrate. Conventionally these include one or more spin coaters SC to deposit a resist layer, one or more developers DE to develop exposed resist, one or more chill plates CH and one or more bake plates BK. A substrate handler, or robot, RO picks up a substrate from input/output ports I/O1, I/O2, moves it between the different process devices and delivers it to the loading bay LB of the lithographic apparatus. These devices, which are often collectively referred to as the track, are under the control of a track control unit TCU which is itself controlled by the supervisory control system SCS, which also controls the lithographic apparatus via lithographic control unit LACU. Thus, the different apparatus may be operated to maximize throughput and processing efficiency.

In order that the substrate that is exposed by the lithographic apparatus is exposed correctly and consistently, it is desirable to inspect an exposed substrate to measure one or more properties such as overlay error between subsequent layers, line thickness, critical dimension (CD), etc. If an error is detected, an adjustment may be made to an exposure of one or more subsequent substrates, especially if the inspection can be done soon and fast enough that another substrate of the same batch is still to be exposed. Also, an already exposed substrate may be stripped and reworked (to improve yield) or discarded, thereby avoiding performing an exposure on a substrate that is known to be faulty. In a case where only some target portions of a substrate are faulty, a further exposure may be performed only on those target portions which are good. Another possibility is to adapt a setting of a subsequent process step to compensate for the error, e.g. the time of a trim etch step can be adjusted to compensate for substrate-to-substrate CD variation resulting from the lithographic process step. In an embodiment, the measurements can be used to enable various configurations (e.g., design, control, modification) of a device manufacturing process (such as a lithographic process) and/or enable various configurations of an object or apparatus using in a manufacturing process.

An inspection apparatus is used to determine one or more properties of a substrate, and in particular, how one or more properties of different substrates or different layers of the same substrate vary from layer to layer and/or across a substrate. The inspection apparatus may be integrated into the lithographic apparatus LA or the lithocell LC or may be a stand-alone device. To enable most rapid measurements, it is desirable that the inspection apparatus measure one or more properties in the exposed resist layer immediately after the exposure. However, the latent image in the resist has a very low contrast—there is only a very small difference in refractive index between the part of the resist which has been exposed to radiation and that which has not—and not all inspection apparatus have sufficient sensitivity to make useful measurements of the latent image. Therefore measurements may be taken after the post-exposure bake step (PEB) which is customarily the first step carried out on an exposed substrate and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibility for rework of a faulty substrate but may still provide useful information, e.g. for the purpose of process control.

A target used by a conventional scatterometer comprises a relatively large periodic structure layout (e.g., comprising one or more gratings), e.g., 40 µm by 40 µm. In that case, the measurement beam often has a spot size that is smaller than the periodic structure layout (i.e., the layout is underfilled such that one or more of the periodic structures is not completely covered by the spot). This simplifies mathematical reconstruction of the target as it can be regarded as infinite. However, for example, so the target can be positioned in among product features, rather than in the scribe lane, the size of a target has been reduced, e.g., to 20 µm by 20 µm or less, or to 10 µm by 10 µm or less. In this situation, the periodic structure layout may be made smaller than the measurement spot (i.e., the periodic structure layout is overfilled). Typically such a target is measured using dark field scatterometry in which the zeroth order of diffraction (corresponding to a specular reflection) is blocked, and only higher orders processed. Examples of dark field metrology can be found in PCT patent application publication nos. WO 2009/078708 and WO 2009/106279, which are hereby incorporated in their entirety by reference. Further developments of the technique have been described in U.S. patent application publications US2011-0027704, US2011-0043791 and US2012-0242970, which are hereby incorporated in their entirety by reference. Diffraction-based overlay (DBO or µDBO) using dark-field detection of the diffraction orders enables overlay measurements on smaller targets. These targets can be smaller than the illumination spot and may be surrounded by product structures on a substrate. In an embodiment, multiple targets can be measured in one image.

In an embodiment, the target on a substrate may comprise one or more 1-D periodic gratings, which are printed such that after development, the bars are formed of solid resist lines. In an embodiment, the target may comprise one or more 2-D periodic gratings, which are printed such that after development, the one or more gratings are formed of solid resist pillars or vias in the resist. The bars, pillars or vias may alternatively be etched into the substrate. The pattern of the grating is sensitive to chromatic aberrations in the lithographic projection apparatus, particularly the projection system PL, and illumination symmetry and the presence of such aberrations will manifest themselves in a variation in the printed grating. Accordingly, the measured data of the printed gratings can be used to reconstruct the gratings. The parameters of the 1-D grating, such as line widths and shapes, or parameters of the 2-D grating, such as pillar or via widths or lengths or shapes, may be input to the reconstruction process, performed by processing unit PU, from knowledge of the printing step and/or other measurement processes.

A metrology apparatus (e.g., dark field metrology apparatus) suitable for use in embodiments of the invention is shown in FIG. 3A. A target T (comprising a periodic structure such as a grating) and diffracted rays are illustrated in more detail in FIG. 3B. The metrology apparatus may be a stand-alone device or incorporated in either the lithographic apparatus LA, e.g., at the measurement station, or the lithographic cell LC. An optical axis, which has several branches throughout the apparatus, is represented by a dotted line O. In this apparatus, radiation emitted by an output 11 (e.g., a source such as a laser or a xenon lamp or an opening connected to a source) is directed onto substrate W via a prism 15 by an optical system comprising lenses 12, 14 and objective lens 16. These lenses are arranged in a double sequence of a 4F arrangement. A different lens arrangement can be used, provided that it still provides a substrate image onto a detector.

In an embodiment, the lens arrangement allows for access of an intermediate pupil-plane for spatial-frequency filtering. Therefore, the angular range at which the radiation is incident on the substrate can be selected by defining a spatial intensity distribution in a plane that presents the spatial spectrum of the substrate plane, here referred to as a (conjugate) pupil plane. In particular, this can be done, for example, by inserting an aperture plate 13 of suitable form between lenses 12 and 14, in a plane which is a back-projected image of the objective lens pupil plane. In the example illustrated, aperture plate 13 has different forms, labeled 13N and 13S, allowing different illumination modes to be selected. The illumination system in the present examples forms an off-axis illumination mode. In the first illumination mode, aperture plate 13N provides off-axis illumination from a direction designated, for the sake of description only, as 'north'. In a second illumination mode, aperture plate 13S is used to provide similar illumination, but from an opposite direction, labeled 'south'. Other modes of illumination are possible by using different apertures. The rest of the pupil plane is desirably dark as any unnecessary radiation outside the desired illumination mode may interfere with the desired measurement signals.

As shown in FIG. 3B, target T is placed with substrate W substantially normal to the optical axis O of objective lens 16. A ray of illumination I impinging on target T from an angle off the axis O gives rise to a zeroth order ray (solid line 0) and two first order rays (dot-chain line +1 and double dot-chain line −1). With an overfilled small target T, these rays are just one of many parallel rays covering the area of the substrate including metrology target T and other features. Since the aperture in plate 13 has a finite width (necessary to admit a useful quantity of radiation), the incident rays I will in fact occupy a range of angles, and the diffracted rays 0 and +1/−1 will be spread out somewhat. According to the point spread function of a small target, each order +1 and −1 will be further spread over a range of angles, not a single ideal ray as shown. Note that the periodic structure pitch and illumination angle can be designed or adjusted so that the first order rays entering the objective lens are closely aligned with the central optical axis. The rays illustrated in FIGS. 3A and 3B are shown somewhat off axis, purely to enable them to be more easily distinguished in the diagram.

At least the 0 and +1 orders diffracted by the target on substrate W are collected by objective lens 16 and directed back through prism 15. Returning to FIG. 3A, both the first and second illumination modes are illustrated, by designating diametrically opposite apertures labeled as north (N) and south (S). When the incident ray I is from the north side of the optical axis, that is when the first illumination mode is applied using aperture plate 13N, the +1 diffracted rays, which are labeled +1(N), enter the objective lens 16. In contrast, when the second illumination mode is applied using aperture plate 13S the −1 diffracted rays (labeled −1(S)) are the ones which enter the lens 16. Thus, in an embodiment, measurement results are obtained by measuring the target twice under certain conditions, e.g., after rotating the target or changing the illumination mode or changing the imaging mode to obtain separately the −1$^{st}$ and the +1$^{st}$ diffraction order intensities. Comparing these intensities for a given target provides a measurement of asymmetry in the target, and asymmetry in the target can be used as an indicator of a parameter of a lithography process, e.g., overlay error. In the situation described above, the illumination mode is changed.

A beam splitter 17 divides the diffracted beams into two measurement branches. In a first measurement branch, optical system 18 forms a diffraction spectrum (pupil plane image) of the target on first sensor 19 (e.g. a CCD or CMOS sensor) using the zeroth and first order diffractive beams. Each diffraction order hits a different point on the sensor, so that image processing can compare and contrast orders. The pupil plane image captured by sensor 19 can be used for focusing the metrology apparatus and/or normalizing intensity measurements of the first order beam. The pupil plane image can also be used for many measurement purposes such as reconstruction, which are not described in detail here.

In the second measurement branch, optical system 20, 22 forms an image of the target on the substrate W on sensor 23 (e.g. a CCD or CMOS sensor). In the second measurement branch, an aperture stop 21 is provided in a plane that is conjugate to the pupil-plane. Aperture stop 21 functions to block the zeroth order diffracted beam so that the image DF of the target formed on sensor 23 is formed from the −1 or +1 first order beam. The images captured by sensors 19 and 23 are output to image processor and controller PU, the function of which will depend on the particular type of measurements being performed. Note that the term 'image' is used here in a broad sense. An image of the periodic structure features (e.g., grating lines) as such will not be formed, if only one of the −1 and +1 orders is present.

The particular forms of aperture plate 13 and stop 21 shown in FIG. 3 are purely examples. In another embodiment, on-axis illumination of the targets is used and an aperture stop with an off-axis aperture is used to pass substantially only one first order of diffracted radiation to the sensor. In yet other embodiments, 2nd, 3rd and higher order beams (not shown in FIG. 3) can be used in measurements, instead of or in addition to the first order beams.

In order to make the illumination adaptable to these different types of measurement, the aperture plate 13 may comprise a number of aperture patterns formed around a disc, which rotates to bring a desired pattern into place. Note that aperture plate 13N or 13S are used to measure a periodic structure of a target oriented in one direction (X or Y depending on the set-up). For measurement of an orthogonal periodic structure, rotation of the target through 90° and 270° might be implemented. Different aperture plates are shown in FIGS. 3C and 3D. FIG. 3C illustrates two further types of off-axis illumination mode. In a first illumination mode of FIG. 3C, aperture plate 13E provides off-axis illumination from a direction designated, for the sake of description only, as 'east' relative to the 'north' previously described. In a second illumination mode of FIG. 3C, aperture plate 13W is used to provide similar illumination, but from an opposite direction, labeled 'west'. FIG. 3D illustrates two further types of off-axis illumination mode. In a first illumination mode of FIG. 3D, aperture plate 13NW provides off-axis illumination from the directions designated 'north' and 'west' as previously described. In a second illumination mode, aperture plate 13SE is used to provide similar illumination, but from an opposite direction, labeled 'south' and 'east' as previously described. The use of these, and numerous other variations and applications of the apparatus are described in, for example, the prior published patent application publications mentioned above.

Figure 7:
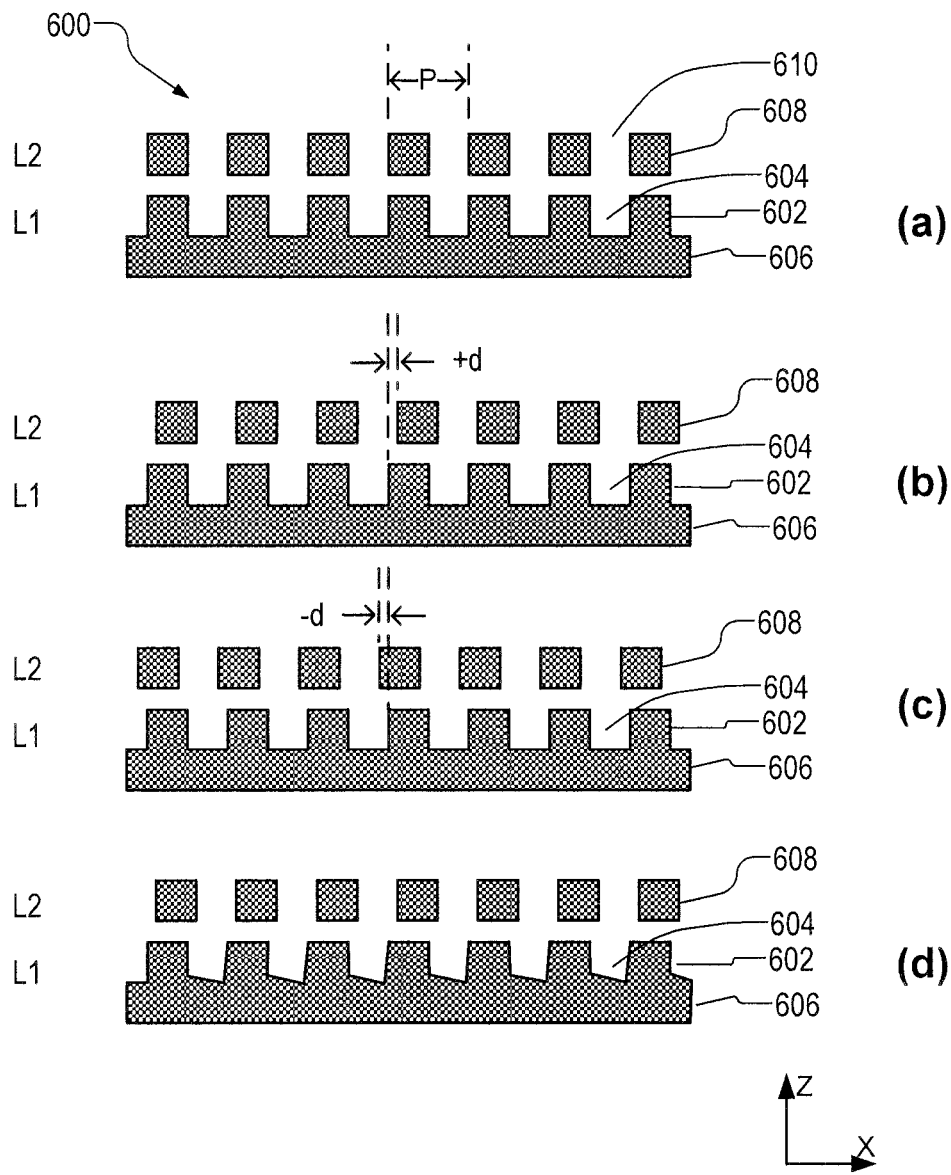
FIG. 7A, FIG. 7B, FIG. 7C and FIG. 7D show schematic cross-sections of overlay periodic structures (e.g., gratings) having different overlay values in the region of zero.

FIG. 4 depicts an example composite metrology target formed on a substrate. The composite target comprises four periodic structures (in this case, gratings) 32, 33, 34, 35 positioned closely together. In an embodiment, the periodic structures are positioned closely together enough so that they all are within a measurement spot 31 formed by the illumination beam of the metrology apparatus. In that case, the four periodic structures thus are all simultaneously illuminated and simultaneously imaged on sensors 19 and 23. In an example dedicated to overlay measurement, periodic structures 32, 33, 34, 35 are themselves composite periodic structures (e.g., composite gratings) formed by overlying periodic structures, i.e., periodic structures are patterned in different layers of the device formed on substrate W and such that at least one periodic structure in one layer overlays at least one periodic structure in a different layer. Such a target may have outer dimensions within 20 μm×20 μm or within 16 μm×16 μm. Further, all the periodic structures are used to measure overlay between a particular pair of layers. To facilitate a target being able to measure more than a single pair of layers, periodic structures 32, 33, 34, 35 may have differently biased overlay offsets in order to facilitate measurement of overlay between different layers in which the different parts of the composite periodic structures are formed. Thus, all the periodic structures for the target on the substrate would be used to measure one pair of layers and all the periodic structures for another same target on the substrate would be used to measure another pair of layers, wherein the different bias facilitates distinguishing between the layer pairs. The meaning of overlay bias will be explained below, particularly with reference to FIG. 7.

FIGS. 7A, 7B and 7C show schematic cross sections of overlay periodic structures (in this case gratings) of respective targets T, with different biases. These can be used on substrate W, as seen in FIGS. 3 and 4. Periodic structures with periodicity in the X direction are shown for the sake of example only. Different combinations of these periodic structures with different biases and with different orientations can be provided.

Starting with FIG. 7A, a composite overlay target 600 formed in two layers, labeled L1 and L2, is depicted. In the lower layer L1, a first periodic structure (in this case a grating) is formed by features (e.g., lines) 602 and spaces 604 on a substrate 606. In layer L2, a second periodic structure (in this case a grating) is formed by features (e.g., lines) 608 and spaces 610. (The cross-section is drawn such that the features 602, 608 extend into the page.) The periodic structure pattern repeats with a pitch P in both layers. Lines 602 and 608 are mentioned for the sake of example only, other types of features such as dots, blocks and via holes can be used. In the situation shown at FIG. 7A, there is no overlay error and no bias, so that each feature 608 lies exactly over a feature 602 in the lower periodic structure (where the measurement is "line-on-line"—in an embodiment, no overlay error may occur where each feature 608 lies exactly over a space 610 wherein the measurement is "line-on-trench").

At FIG. 7B, the same target with a bias +d is depicted such that the features 608 of the upper periodic structure are shifted by a distance d to the right (the distance d being less than the pitch P), relative to the features 602 of the lower periodic structures. That is, features 608 and features 602 are arranged so that if they were both printed exactly at their nominal locations, features 608 would be offset relative to the features 602 by the distance d. The bias distance d might be a few nanometers in practice, for example 10 nm-20 nm, while the pitch P is for example in the range 300-1000 nm, for example 500 nm or 600 nm. At FIG. 7C, the same target with a bias −d is depicted such that the features 608 are shifted to the left relative to the features 602. Biased targets of this type shown at FIGS. 7A to 7C, and their use in measurement, are described in, for example, the patent application publications mentioned above.

Further, as alluded to above, while FIGS. 7A-7C depicts the features 608 lying over the features 602 (with or without a small bias of +d or −d applied), which is referred to as a "line on line" target having a bias in the region of zero, a target may have a programmed bias of P/2, that is half the pitch, such that each feature 608 in the upper periodic structure lies over a space 604 in the lower periodic structure. This is referred to as a "line on trench" target. In this case, a small bias of +d or −d may also be applied. The choice between "line on line" target or a "line on trench" target depends on the application.

Returning to FIG. 4, periodic structures 32, 33, 34, 35 may also differ in their orientation, as shown, so as to diffract incoming radiation in X and Y directions. In one example, periodic structures 32 and 34 are X-direction periodic structures with biases of +d, −d, respectively. Periodic structures 33 and 35 may be Y-direction periodic structures with offsets +d and −d respectively. While four periodic structures are illustrated, another embodiment may include a larger matrix to obtain desired accuracy. For example, a 3×3 array of nine composite periodic structures may have biases −4d, −3d, −2d, −d, 0, +d, +2d, +3d, +4d. Separate images of these periodic structures can be identified in the image captured by sensor 23.

FIG. 5 shows an example of an image that may be formed on and detected by the sensor 23, using the target of FIG. 4 in the apparatus of FIG. 3, using the aperture plates 13NW or 13SE from FIG. 3D. While the sensor 19 cannot resolve the different individual periodic structures 32 to 35, the sensor 23 can do so. The dark rectangle represents the field of the image on the sensor, within which the illuminated spot 31 on the substrate is imaged into a corresponding circular area 41. Within this, rectangular areas 42-45 represent the images of the periodic structures 32 to 35. If the periodic structures are located in product areas, product features may also be visible in the periphery of this image field. Image processor and controller PU processes these images using pattern recognition to identify the separate images 42 to 45 of periodic structures 32 to 35. In this way, the images do not have to be aligned very precisely at a specific location within the sensor frame, which greatly improves throughput of the measuring apparatus as a whole.

Once the separate images of the periodic structures have been identified, the intensities of those individual images can be measured, e.g., by averaging or summing selected pixel intensity values within the identified areas. Intensities and/or other properties of the images can be compared with one another. These results can be combined to measure different parameters of the lithographic process. Overlay performance is an example of such a parameter.

Figure 6:
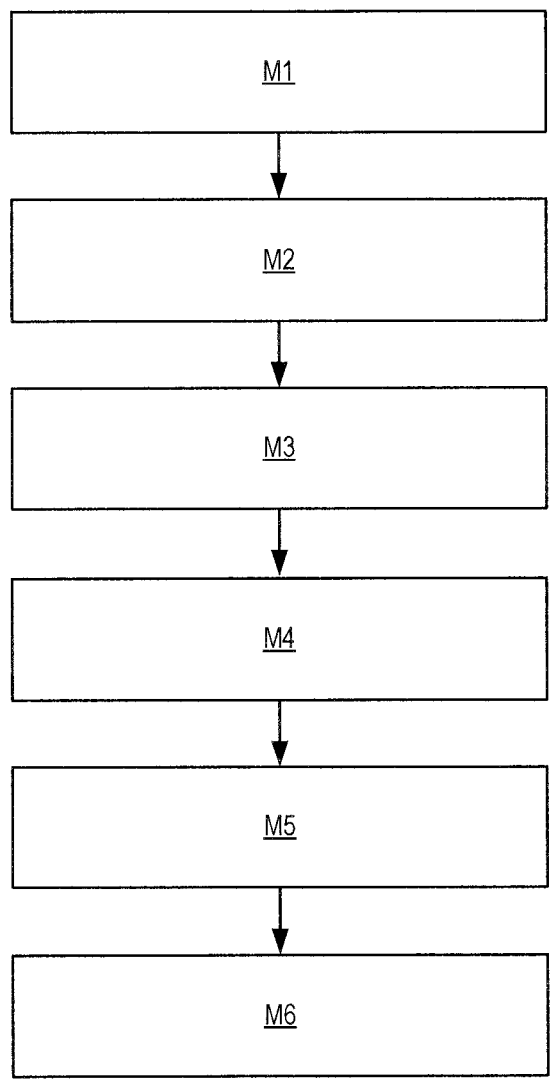
FIG. 6 is a flowchart showing the steps of an overlay measurement method using the apparatus of FIG. 3 and adaptable to embodiments of the present invention.

FIG. 6 illustrates how, using for example the method described in PCT patent application publication no. WO 2011/012624, which is incorporated herein in its entirety by reference, overlay error between the two layers containing the component periodic structures 32 to 35 is measured through asymmetry of the periodic structures, as revealed by comparing their intensities in the +1 order and −1 order dark field images. At step M1, the substrate, for example a semiconductor wafer, is processed through the lithographic cell of FIG. 2 one or more times, to create a structure including the target comprising periodic structures 32-35. At M2, using the metrology apparatus of, e.g., FIG. 3, an image of the periodic structures 32 to 35 is obtained using one of the first order diffracted beams (say −1). In an embodiment, a first illumination mode (e.g., the illumination mode created using aperture plate 13NW) is used. Then, whether by, for example, changing the illumination mode, or changing the imaging mode, or by rotating substrate W by 180° in the field of view of the metrology apparatus, a second image of the periodic structures using the other first order diffracted beam (+1) can be obtained (step M3). Consequently, the +1 diffracted radiation is captured in the second image. In an embodiment, the illuminated mode is changed and a second illumination mode (e.g., the illumination mode created using aperture plate 13SE) is used. In an embodiment, tool-induced artifacts like tool induced shift (TIS) can be removed by doing the measurement at 0° and 180° substrate orientation.

Note that, by including only half of the first order diffracted radiation in each image, the 'images' referred to here are not conventional dark field microscopy images. The individual periodic structure features are not resolved. Each periodic structure will be represented simply by an area of a certain intensity level. In step M4, a region of interest (ROI) is identified within the image of each component periodic structure, from which intensity levels will be measured.

Having identified the region of interest P1, P2, P3, P4 for each respective individual periodic structure 32-35 and measured its intensity, the asymmetry of the periodic structure, and hence, e.g., overlay error, can then be determined. This is done by the image processor and controller PU in step M5 comparing the intensity values obtained for +1 and −1 orders for each periodic structure 32-35 to identify any difference in their intensity, i.e., an asymmetry. The term "difference" is not intended to refer only to subtraction. Differences may be calculated in ratio form. In step M6 the measured asymmetries for a number of periodic structures are used together with, if applicable, knowledge of the overlay biases of those periodic structures to calculate one or more performance parameters of the lithographic process in the vicinity of the target T. A performance parameter of interest is overlay. Other parameters of performance of the lithographic process can be calculated such as focus and/or dose. The one or more performance parameters can be fed back for improvement, design, etc. of the lithographic process, used to improve the measurement and calculation process of FIG. 6 itself, used to improve the design of the target T, etc.

Figure 8:
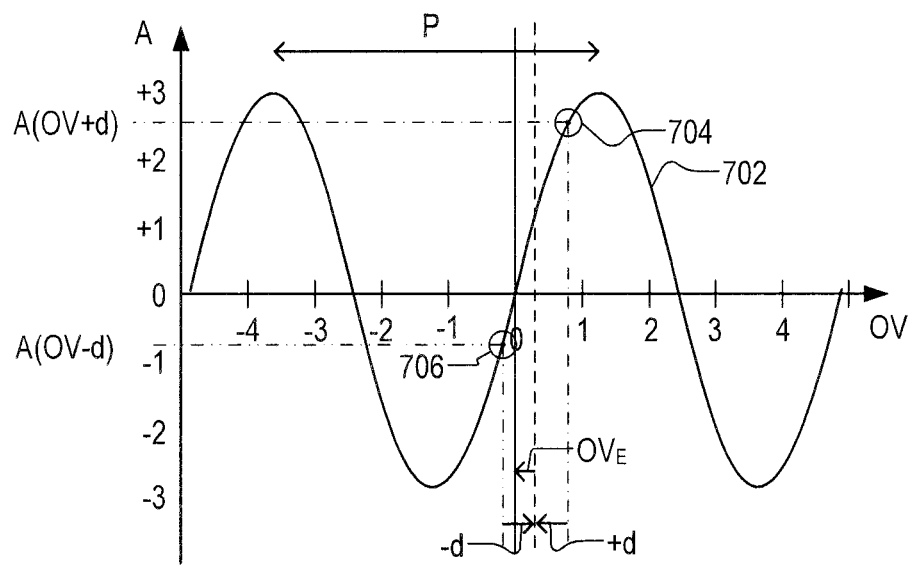
FIG. 8 illustrates principles of overlay measurement in an ideal target structure.

In an embodiment to determine overlay, FIG. 8 depicts a curve 702 that illustrates the relationship between overlay error OV and measured asymmetry A for an 'ideal' target having zero offset and no structural asymmetry within the individual periodic structures forming the overlay target. These graphs are to illustrate the principles of determining the overlay only, and in each graph, the units of measured asymmetry A and overlay error OV are arbitrary.

In the 'ideal' situation of FIGS. 7A-7C, the curve 702 indicates that the measured asymmetry A has a sinusoidal relationship with the overlay. The period P of the sinusoidal variation corresponds to the period (pitch) of the periodic structures, converted of course to an appropriate scale. The sinusoidal form is pure in this example, but can include harmonics in real circumstances. For the sake of simplicity, it is assumed in this example (a) that only first order diffracted radiation from the target reaches the image sensor 23 (or its equivalent in a given embodiment), and (b) that the experimental target design is such that within these first orders a pure sine-relation exists between intensity and overlay between upper and lower periodic structures results. Whether this is true in practice is a function of the optical system design, the wavelength of the illuminating radiation and the pitch P of the periodic structure, and the design and stack (i.e., the one or more layers of material making up the target) of the target.

As mentioned above, biased periodic structures can be used to measure overlay, rather than relying on a single measurement. This bias has a known value defined in the patterning device (e.g. a reticle) from which it was made, that serves as an on-substrate calibration of the overlay corresponding to the measured signal. In the drawing, the calculation is illustrated graphically. In steps M1-M5 of FIG. 6, asymmetry measurements A(+d) and A(−d) are obtained for component periodic structures having biases +d and −d respectively (as shown in FIGS. 7B and 7C, for example). Fitting these measurements to the sinusoidal curve gives points 704 and 706 as shown. Knowing the biases, the true overlay error OV can be calculated. The pitch P of the sinusoidal curve is known from the design of the target. The vertical scale of the curve 702 is not known to start with, but is an unknown factor which is called an overlay proportionality constant, K.

In equation terms, the relationship between overlay and measured asymmetry A may be assumed to be:

$$A = K\sin(OV) \quad (1)$$

where OV is expressed on a scale such that the periodic structure pitch P corresponds to an angle 2π radians. Using two measurements with periodic structures with different, known biases to arrive at two values of A, one can solve two equations to calculate the unknowns K and overlay OV.

Although these measurement techniques are fast and relatively computationally simple (once calibrated), they rely on an assumption that the overlay/lateral shift is the only cause of asymmetry. That is, it assumes an 'ideal' situation with, for example, no structural asymmetry in the target. Any structural asymmetry in the stack, such as asymmetry of features within one or both of the overlaid periodic structures, also causes an asymmetry in the $1^{st}$ orders besides the overlay/lateral shift. This structural asymmetry which is not related to the overlay clearly perturbs the measurement, giving an inaccurate result.

As an example of structural asymmetry, one or more of the periodic structures of the target may be structurally deformed. For example, one or more side walls of periodic structure features (e.g., grating lines) of the target may not be vertical as intended. As another example, one or spaces between periodic structure features (e.g., grating spaces of trenches) of a target may be larger or smaller than as intended. Further, one or more features of a periodic structure of a target (e.g., grating lines) may have a smaller or larger width than as intended. Additionally, even where a difference from intended is uniform for one or more periodic structures of the target, that difference from intended may not be the same as for one or more other periodic structures of the target. Structural asymmetry in the lower periodic structure of a composite target is a common form of structural asymmetry. It may originate, for example, in a substrate processing steps such as chemical-mechanical polishing (CMP), performed after the lower periodic structure was originally formed.

Referring to FIG. 7D, an example of structural asymmetry of a lower periodic structure is schematically depicted. The features and spaces in the periodic structures at FIGS. 7A to 7C are shown as perfectly square-sided, when a real feature and space would have some slope on a surface, and a certain roughness. Nevertheless they are intended to be at least symmetrical in profile. The features 602 and/or spaces 604 at FIG. 7D in the lower periodic structure no longer have a symmetrical form at all, but rather have become distorted by, for example, one or more processing steps. Thus, for example, a bottom surface of each space 604 has become tilted. Side wall angles of the features and spaces have become asymmetrical also. When overlay is measured by the method of FIG. 6 using only two biased periodic structures, the structural asymmetry cannot be distinguished from overlay, and overlay measurements become unreliable as a result.

Thus, accuracy in measurement (e.g., measurement of alignment where the target is used for alignment, measurement of overlay where the target is used for overlay measurement, etc.) can be significantly reduced by asymmetric structural deformation of one or more periodic structures (e.g., gratings) of the target. The measurement errors that arise from structural asymmetry may be corrected with changes to the process of creating or measuring the targets (e.g., process offsets) which are, for example, based on yield (i.e., evaluation of processed devices to determine whether the target was accurate) or cross-sections of the target. However, these methods can be destructive. They may only be effective to correct a constant asymmetry-induced process error. But, variation in structural asymmetry of the target is not effectively solved by cross-sections or yield measurements. Accordingly, there is a desire for, for example, a robust solution of evaluating and correcting for structural asymmetry that overcomes one or more of these or other limitations.

Therefore, it is desired to distinguish the contributions to measured target asymmetry that are caused by overlay and other effects in an improved way, and in particular which allow the actual geometries to be quantified. As such, rather than simply measuring the effect of the asymmetry on the overlay measurement and correcting for this, embodiments in this disclosure enable the actual shape of the target (and therefore the actual asymmetries) to be determined, without, e.g., the need for a full, angle-resolved reconstruction. The methods described herein also enable the "true overlay", i.e., overlay without the effect of geometric structural asymmetry of the periodic structures to be directly reconstructed from (dark-field) measurements. This is in contrast to overlay being determined using methods such as described in PCT patent application publication no. WO2016-083076, where an intensity asymmetry measurement (which includes contributions due to the structural asymmetry) is made and then these contributions are corrected for by quantifying and removing the effect of the structural asymmetry from the overlay measurements. The methods described herein enable the simultaneous reconstruction of the true overlay and one or more of the geometric asymmetry parameters of the upper and/or lower periodic structure. This fundamentally improves the precision and accuracy with which the true overlay can be estimated. In addition, the ability to directly reconstruct the true overlay can significantly help in improving both the fabrication process as well as production yield.

Other variations in one or more various process parameters, which do not necessarily result in structural asymmetry, can have a significant impact on a target. Such process parameters may include layer height/thickness (e.g., of a device layer or a resist layer, etch depth), and/or critical dimension (CD) or refractive index (of a device layer or a resist layer). For example, the ability to measure layer heights (i.e., layer thicknesses) can improve process control during fabrication. Accurate measurement of the layer heights can also enable a more robust recipe selection for measuring other parameters of interest (e.g., overlay). Presently layer thicknesses are optically estimated using multiple thin-film targets (with no periodic structures present). However, this can use valuable additional area on the substrate, and additional time to perform the measurements.

Therefore a proposed measurement technique is disclosed that comprises performing a measurement and reconstruction of a target using higher order radiation diffracted from the target. In alternative embodiments, the measurement may be performed in either the pupil plane, or image plane, the image plane being a plane where the image of the target is formed. Measurement in the pupil plane shares many similarities with present CD reconstruction techniques, except in the embodiments here the measurements are performed on multiple layer targets. However, present CD reconstruction techniques are performed on periodic structures with a larger pitch than the (for example) overlay targets described here. Because of this larger pitch, it is normally only possible to capture the zeroth order (specularly reflected) radiation. However, using the techniques described herein on smaller overlay targets, the wavelength-to-pitch ratio (which determines the diffraction angles) is such that it is possible to capture higher orders (at least the +1/−1 orders and possibly additionally other higher orders). The overlay targets may be no larger than 20 μm or no larger than 10 μm in either dimension in the substrate plane (e.g. X or Y). Performing a reconstruction using the higher orders (in addition to the zeroth order) means that the measurement has increased sensitivity to parameter changes and therefore a more complex model with a greater number of parameters (and specifically floated parameters) can be used. However, it is measurement in the image plane (in a similar manner to dark-field metrology techniques such as diffraction based overlay as described above) which brings the greater benefits. Therefore, without being limited to such, this disclosure will principally describe image plane measurements and techniques.

A reconstruction technique is described which enables modelling of a stack geometry. Such a stack geometry may comprise the geometry of, for example, a target comprising two periodic structures (e.g., gratings) in different layers on a substrate. In particular, the targets may be of a form illustrated in FIG. 4 and FIGS. 7B to 7D, comprising at least a pair of periodic structures, a first periodic structure comprising a first offset (e.g. +d) in the relative position between its constituent periodic structure (e.g., gratings) and a second periodic structure comprising a second offset (e.g.−d) in the relative position between its constituent periodic structures (e.g., gratings). The proposed reconstruction technique will enable values for one or more geometric parameters, in addition to overlay, to be found. Such geometric parameters may comprise one or more layer heights of the target (i.e., in the target stack). The one or more layers for which a layer height can be determined by such a method may comprise and/or number more than only the layers comprising the target periodic structure. That is, there may be one or more additional layers above and/or below the target and/or one or more additional intervening layers between the periodic structure for which a layer height can be measured. These one or more layers are considered to be part of the target.

Figure 9:
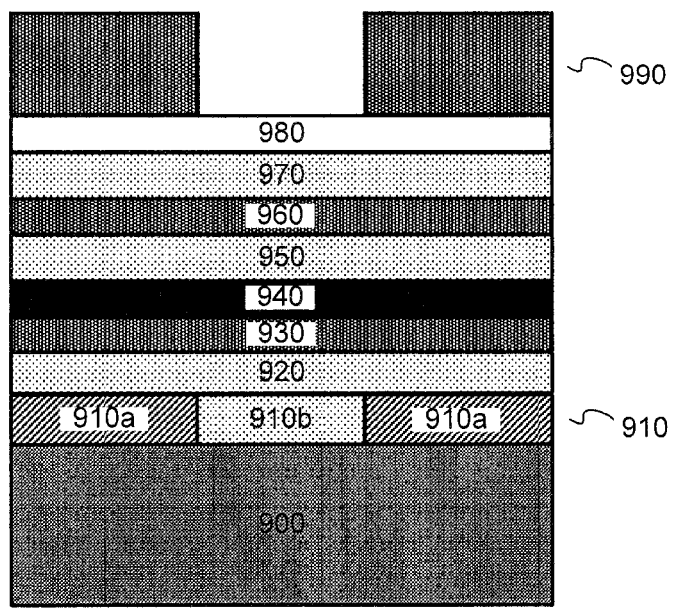
FIG. 9 is an example stack showing the different layers which may be comprised in a target.

FIG. 9 shows an example overlay target showing the different layers which may be present within a stack. Layer 900 is the actual substrate onto which the target is formed. Layer 910 is a lower periodic structure layer (comprising for example polysilicon "lines" 910a and interlayer dielectric ILD "spaces" 910b). Layers 920 to 980 are intervening layers which may (in this specific example) include an ILD layer 920, a silicon carbide layer 930, a titanium nitride layer 940, oxide layers 950, 970, a carbon layer 960 and a BARC (bottom anti-reflective coating) layer 980. Finally, layer 990 comprises an upper periodic structure layer (in resist). The methods described herein enable a layer height for some or all of these layers to be determined, and in particular by having each of a plurality of these layer heights to be floated parameters in a single reconstruction.

One or more other geometric parameters which may be determined using methods described herein include, for example, critical dimension (e.g. mid-CD), floor tilt, top tilt and/or side wall angle (SWA)—left and/or right—in each case of either or both of the upper periodic structure and/or the lower periodic structure. Many of the geometric parameters which can be determined using the methods herein are structural asymmetry parameters (e.g., floor tilt, top tilt and/or SWA differences between left and right walls), which are known to negatively impact on overlay measurements using dark field techniques. The methods described herein allow determination of overlay, free from the effect of structural asymmetry, and additionally one or more or all of these actual structural asymmetry parameters, which can also be used in quality control, for example.

Figure 10:
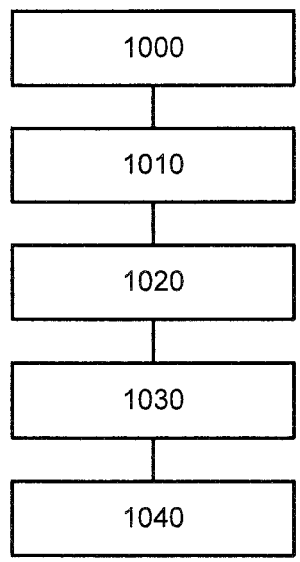
FIG. 10 is a flowchart describing a method according to an embodiment of the invention.

FIG. 10 is a flowchart describing such a method. At step 1000, a measurement of a structure is performed to obtain a measured response of the target (measurement data). The structure may comprise a target as described, having overlaid periodic structures and at least two periodic structures of different biases (e.g., +d and −d). In a an embodiment, the measurement is performed as a field measurement, in the image plane, although a pupil measurement is also possible within the scope of this disclosure.

At step 1010 a 'model recipe' is established, which defines a parameterized model of the target in terms of a number of parameters which include one or more geometric parameters of the target, as described. The model recipe may additionally include one or more other "measurement parameters" such as a parameter of the measurement radiation used, which will also affect the target response. One or more properties of the target material and/or of one or more underlying layers are also represented by one or more parameters such as refractive index (at a particular wavelength present in the measurement radiation beam) and dispersion models.

While a target may be defined by dozens of parameters describing its shape and material properties, the model recipe will define many of these to have fixed values, while others are to be variable or 'floating' parameters for the purpose of this disclosure. These floating parameters may comprise many of the geometric parameters (e.g., overlay CD, SWA and/or tilt) whose values are desired, and possibly one or more other parameters—referred sometimes as a nuisance parameter—which cannot be fixed and therefore need to be solved for, but are of little interest beyond the reconstruction. Further below, there is described a process by which the choice between fixed and floating parameters may be made. One or more other parameters may be permitted to vary in only a limited extent without being fully independent floating parameters. It is notable that in the reconstruction methods described herein, a large number of parameters may be floated and/or fixed at nominal values while still providing good estimations for one or more floated parameters of interest.

At step 1020, a modeled response of the target (simulated data) is obtained by simulating the scattering properties of the target defined by the model recipe, for example using a rigorous optical diffraction method such as RCWA or a solver of Maxwell equations. Any suitable scatterometry model may be used, including vector or scalar models. In an embodiment, a point spread function (PSF) model may be used. A PSF model has an advantage of being relatively fast and simple, without needing to model the optical path, nor needing a graphics processing unit. It may be noted that the PSF model does not simulate per pixel intensity in the image plane. Instead, the model uses Parseval's theorem (energy conservation) to compute the average intensity in the image plane based on the intensities in the pupil plane. The average (grey level) intensity in the image plane may be obtained by accounting for wavelength dependent CCD integration time, to which measurement apparatus camera noise may (optionally) also be added.

The total number of simulated average intensities to be generated may comprise the product of the number of measurement radiation characteristics (e.g., wavelengths and polarizations), the number of captured diffraction orders and the number of target biases. By way of illustration, in an example where the measurement radiation is comprised of 7 wavelengths and 2 polarizations, and there are 2 captured orders (+1 and −1) and 2 biases (+d and −d), the number of intensities (e.g., the length of an intensities vector) will be 7×2×2×2=56.

At step 1030, an objective function is devised which minimizes the difference between measured response and modeled response. This objective function is then minimized in terms of the floating parameters (step 1040). The minimization may be iterative (i.e., varying one or more of the floating parameters and repeating step 1020 to obtain an updated modeled response, in a number of iterations until convergence on a solution to a desired accuracy). Alternatively, or in addition this step may use the results of a previously modeled library of modeled responses for comparison to the measured response. For example, a library search for a coarse set of parameters may be performed initially, followed by one or more iterations using the objective function to determine a more accurate set of parameters to report the parameters of the target with a desired accuracy.

The objective function can be based on any intensity based metric, which may include, for example:

i) a scaled image intensity asymmetry based metric, ii) stack sensitivity based metric; or iii) raw average ROI image intensity based metric.

Each of the examples i), ii) and iii) above show better results for some applications than for other applications. For example, the stack-sensitivity based objective function may be better suited to reconstruct the one or more layer heights in a substrate stack, in particular, when no asymmetry parameters are also floated. On the other hand, the use of a scaled image intensity asymmetry based objective function may be desirable when reconstructing one or more geometric shape asymmetries in the presence of one or more machine calibration errors. Both of examples i) and ii) are self-calibrating and therefore do not require model calibration. A raw average ROI image intensities based objective function is most useful when it is desirable to minimize the amount of measured data required to obtain the one or more parameters of interest, for example by using measurement radiation of only a single wavelength and polarization. In case raw average ROI image intensities are used, a model calibration would be performed if more than one wavelength/polarization were used.

For a scaled image intensity asymmetry based metric, the scaled image intensity asymmetries $A(+d)_{scaled}$, $A(-d)_{scaled}$ may be calculated as:

$$A(+d)_{scaled} = \frac{I_{+d}^{+1} - I_{+d}^{-1}}{(I_{+d}^{+1} + I_{+d}^{-1})/2}$$

$$A(-d)_{scaled} = \frac{I_{-d}^{+1} - I_{-d}^{-1}}{(I_{-d}^{+1} + I_{-d}^{-1})/2}$$

where each/term is a measured intensity of a diffraction order with each subscript denoting the bias and each superscript denoting the diffraction order, such that $I_{+d}^{+1}$ is the measured intensity of the +1 diffraction order from the +d biased periodic structure.

For a raw average ROI image intensity based metric, the raw average ROI image intensity S may be calculated as:

$$S = \tfrac{1}{4}[(I_{+d}^{+1} + I_{+d}^{-1}) + (I_{-d}^{+1} + I_{-d}^{-1})]$$

For a stack sensitivity based metric, the stack sensitivity SS (also called signal contrast) can be understood as a measurement of how much the intensity of the signal changes as overlay changes because of diffraction between target (e.g., periodic structure) layers. That is, in an overlay context, it describes the contrast between upper and lower periodic structures of an overlay target and thus represents a balance between diffraction efficiencies between the upper and lower periodic structures. It is thus an example measure of sensitivity of the measurement. It may be calculated as the ratio of the overlay proportionality constant K to average intensity S:

$$SS = \frac{K}{S}$$

where:

-continued
$$K = \frac{(I_{+d}^{+1} - I_{+d}^{-1}) - (I_{-d}^{+1} - I_{-d}^{-1})}{2d}$$

In each case, the objective function may take the form of:

$$\hat{p} = \underset{p}{\mathrm{argmin}}(p - \mu)^T C_{prior}^{-1}(p - \mu) + (I_f - M_f(p))^T C_F^{-1}(I_f - M_f(p))$$

where $C_{prior}$ is a diagonal matrix with Bayesian prior variances (variances may be set to be large—in the order of 10). $I_f$ is the set of experimental intensity metric values (e.g., measured diffraction based intensity values, scaled asymmetries or stack sensitivities), $M_f$ is the set of modeled intensity metric values, $\mu$ are nominal parameter values and (optionally) $C_F$ is a noise matrix based on the measurement apparatus detector (e.g., camera) noise.

As stated above, scaled intensity asymmetry based reconstruction may be desirable for reconstructing one or more geometric shape asymmetries while stack sensitivity based reconstruction may be desired for reconstructing one or more layer heights (without reconstructing geometric shape asymmetries). Consequently, in an embodiment, a two-stage reconstruction may be performed. In a first stage, only one or more layer heights are reconstructed (floated parameter(s)) with the other parameters being fixed. This first stage is performed using a stack-sensitivity based objective function. In a second stage, the one or more determined layer heights are fed forward as fixed parameter(s) in a second reconstruction for one or more geometric shape asymmetries (e.g., floor/top tilt, SWA, overlay, etc.), and optionally a CD metric, using a scaled intensity asymmetry objective function. In a specific embodiment, the one or more determined layer heights from the first stage can be used to predict a stack height variation map which describes the variation of the one or more layer heights across the substrate. This stack height variation map can then be used to fix the one or more layer heights in the second stage reconstruction. This enables a full reconstruction of all parameters of interest to be performed, including for example overlay error (free of the effects of other geometric shape asymmetries) and layer heights, using an existing metrology device (such as illustrated in FIG. 3A) and with no additional measurement cost (since, e.g., diffraction based overlay measurements are typically performed in any case to measure overlay using existing diffraction based overlay techniques).

Figure 11:
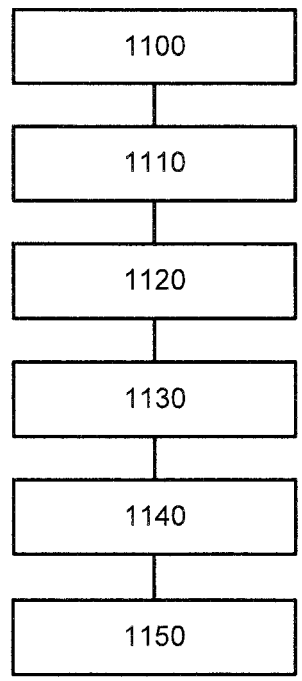
FIG. 11 is a flowchart describing a method according to an embodiment of the invention.

It is further proposed, in an embodiment, to have a reconstruction optimization step. Such a step can be used to determine which parameters should be fixed and which may be floated in a reconstruction as described. FIG. 11 is a flowchart describing such a method. At step 1100, a derivative of the objective function with respect to each reconstruction parameter is found at different sampling locations within the parameters domain. The conditionality of the resultant derivative matrix is determined at step 1110. An angle between different groups of parameters is also determined. At step 1120, the conditionality and/or the angle(s) are used to identify whether any one or more pairs (or larger groups) of reconstruction parameters are highly correlated (e.g., show a high degree of multicollinearity). At step 1130, the obtained derivatives may be used to identify those one or more reconstruction parameters which do not cause a significant change in the objective function. At step 1140, it is determined which one or more parameters should be fixed. These may include those determined at step 1130 to not cause significant change in the objective function, and/or a relatively less important parameter(s) of any correlated pair/group identified at step 1120. Steps 1120 to 1140 may comprise determining the conditionality and angle of the derivative matrix with respect to a particular parameter or parameters. For example, if the derivative matrix is determined to be ill-conditioned (e.g., based on a threshold condition number) with respect to a particular parameter, or if a parameter is collinear with other parameters then that parameter may be fixed. If two or more of the parameters related to the high condition number have high proportions of variance, this may indicate high correlation. One or more well-conditioned parameters may be chosen to be floated in the reconstruction. At step 1150, the obtained derivatives can be used to attach Bayesian priors to the one or more floated parameters.

In an embodiment, measurement recipe selection may be optimized. In such an embodiment, layer thicknesses may be determined by reconstruction as described, and a stack height variation map based on the layer thicknesses may then be used in finding the most appropriate wavelength/polarization combination for a robust overlay, via swing curves. A swing curve may be a curve fitted through a spectral sequence (e.g., variation through wavelength) of an intensity parameter such as overlay proportionality K or stack sensitivity. As will be appreciated, a graph need not be generated as just the data can be processed. Measurement recipe selection may be made on the basis of such swing curves, e.g., to optimize stack sensitivity. The swing curve changes as a function of changes in layer thickness. If the layer thickness variation is not taken into account when choosing a wavelength/polarization combination for overlay measurement, then the unaccounted for thickness variations could cause the stack to be insufficiently sensitive to a change in overlay for the chosen recipe, since an incorrect position on the swing curve could then be erroneously chosen. In that case, the measured overlay will be neither precise nor accurate. By using the reconstructed stack height variation map, the correct swing curve can be generated. The wavelength/polarization recipe can then be chosen at a robust and correct position based on this correct swing curve so that the sensitivity to overlay is optimal, despite the thickness variations.

In summary, by using overlapping periodic structures to estimate a stack height of different layers on the substrate, it is possible to avoid the use of multiple thin films (with no periodic structures present) to optically estimate the layer heights. This also means that valuable substrate area is not used by such multiple thin film targets. Knowledge of the estimated layer heights in the stack can help improve process control during fabrication.

No hardware changes need be implemented to many existing metrology systems to allow estimation of stack heights, true overlay (free of geometrical asymmetry effects), and values for actual geometric shape asymmetries. This fundamentally improves the precision and accuracy with which the true overlay can be estimated. The ability to measure the true overlay can help significantly in improving both the fabrication process as well as the yield.

The reconstruction of asymmetry parameters will provide estimates of CD, SWA and/or tilt in the periodic structure(s) of the target. These parameters can also provide insights into the accuracy of different processing steps (etch, develop, CMP, etc.) in the fabrication. These are effectively all obtained 'for free' since the image plane response needed for reconstruction is already measured for calculating overlay.

Since the methods described herein employ an average intensity of all the pixels within the ROI in the image plane response, the signal-to-noise ratio of the objective function is very high. The reconstruction algorithms therefore do not suffer significantly from the impact of noise when floating many parameters. This means that many parameters can be estimated with limited measured data.

Those measurements made using the target naturally may be used in creating, for example, devices by a lithographic process. Further, besides being used to correct measurements made using the target, the measure of the asymmetric deformation of the target may be used in the (re-)design of the target (e.g., making a change to a layout of the design), may be used in the process of forming the target (e.g., making a change in material, a change in printing steps or conditions, etc.), may be used in formulation of the measurement conditions (e.g., make a change in the optical measurement formulation in terms of wavelength, polarization, illumination mode, etc. of the measurement beam), may be used in configuration (e.g., design, control, modification, etc.) of a manufacturing process, may be used in configuration (e.g., design, control, modification, etc.) of an apparatus or object for a manufacturing process, etc.

Further embodiments are further described in below numbered clauses:

1. A metrology method comprising:
   obtaining measurement data relating to a measurement of a target formed in at least two layers on a substrate by a lithographic process, the measurement data being derived from at least one corresponding pair of non-zeroth diffraction orders;
   obtaining simulation data relating to simulation of a measurement of the target as defined in terms of geometric parameters of the target, the geometric parameters comprising one or more variable geometric parameters; and
   minimizing a difference between the measurement data and simulation data, so as to directly reconstruct values for the one or more variable geometric parameters.
2. A method according to clause 1, wherein the measurement data relates to a measurement of the target derived from a dark-field measurement and wherein the at least one corresponding pair of non-zeroth diffraction orders is detected in an image plane.
3. A method according to clause 2, wherein the minimizing step is performed to minimize the difference between the measurement data and simulation in terms of an intensity metric of the detected non-zeroth diffraction orders.
4. A method according to clause 3, wherein the measurement data and simulation data each comprises a plurality of intensity values, one for each combination of non-zeroth diffraction order, measurement radiation characteristic, and/or imposed target bias comprised in the target, and the intensity metric is derived from the intensity values.
5. A method according to clause 3 or clause 4, wherein the intensity metric comprises scaled image intensity asymmetry, the scaled image intensity asymmetry comprises an intensity difference between corresponding pairs of non-zeroth diffraction orders scaled by their average intensity.
6. A method according to clause 3 or clause 4, wherein the intensity metric comprises stack sensitivity, wherein stack sensitivity is the ratio of an overlay proportionality constant to an average of the intensities of regions of interest within the measurement image.
7. A method according to clause 3 or clause 4, wherein the intensity metric comprises average intensity, average intensity being an average of the intensities of regions of interest within the measurement image.
8. A method according to clause 1, wherein the measurement data relates to a measurement of the target derived from a pupil-plane measurement and wherein the at least one corresponding pair of non-zeroth diffraction orders is detected in the pupil plane.
9. A method according to any preceding clause, wherein the one or more variable geometric parameters comprise at least one layer height of a layer comprised in the target.
10. A method according to clause 9, wherein the one or more variable geometric parameters comprise a plurality of layer heights of different layers comprised in the target, and wherein the minimization step comprises simultaneously reconstructing values for the plurality of layer heights.
11. A method according to clause 9 or clause 10, comprising calculating a spectral sequence describing a variation of an intensity parameter with wavelength of measurement radiation for the target with the at least one layer height as determined in the minimization step; and optimizing the measurement radiation based on the spectral sequence.
12. A method according to any preceding clause, wherein the one or more variable geometric parameters comprise overlay error absent of the effects of geometric asymmetry in at least one of the structures comprised in the target.
13. A method according to any preceding clause, wherein the one or more variable geometric parameters comprise one or more geometric asymmetry parameters of at least one of the structures comprised in the target.
14. A method according to any of clauses 1 to 7, wherein the one or more variable geometric parameters comprise:
   one or more layer heights of layers comprised in the target; and
   one or more other variable geometric parameters which may comprise one or more selected from: overlay error absent of the effects of geometric asymmetry in at least one of the structures comprised in the target and/or one or more geometric asymmetry parameters,
   wherein the minimization step is performed in two stages, a first stage for reconstructing values for the one or more layer heights and a second stage for reconstructing values for the one or more other variable geometric parameters, the one or more layer heights determined in the first stage being fed forward as one or more fixed layer height parameters in the second stage.
15. A method according to clause 14, wherein the intensity metric comprises stack sensitivity in the first stage, wherein stack sensitivity is the ratio of the overlay proportionality constant to an average of the intensities of regions of interest within the measurement image; and wherein the intensity metric comprises scaled image intensity asymmetry in the second stage, scaled image intensity asymmetry comprising the intensity difference between corresponding pairs of non-zeroth diffraction orders scaled by their average intensity.
16. A method according to clause 14 or clause 15, wherein the first stage is used to predict a stack height variation map which describes the variation of the layer heights across the substrate, the stack height variation map being used to determine the one or more fixed layer height parameters in the second stage.
17. A method according to any of clauses 14 to 16, comprising calculating a spectral sequence describing a variation of an intensity parameter with wavelength of measurement radiation for the target with the at least one layer height as determined in the minimization step; and optimizing the measurement radiation based on the spectral sequence.

18. A method according to any of clauses 13 to 17, wherein the one or more geometric asymmetry parameters comprise one or more selected from: floor tilt, top tilt, side wall angle, and/or critical dimension.

19. A method according to any preceding clause, wherein the minimization step comprises devising an objective function for minimizing the difference between the measurement data and the simulation data.

20. A method according to clause 19, wherein the objective function comprises a term which accounts for detector noise.

21. A method according to clause 19 or claim 20, further comprising a reconstruction optimization step to determine which of the geometric parameters should be the variable geometric parameters.

22. A method according to clause 21, comprising, with respect to each geometric parameter, performing the steps of:
determining a derivative matrix of the objective function; and
determining which of the geometric parameters should be the variable geometric parameters based on the conditionality of the derivative matrix and angles of different vector(s) combinations within the derivative matrix.

23. A method according to clause 22, wherein the reconstruction optimization step comprises not selecting a geometric parameter to be a variable geometric parameter if the corresponding derivative matrix is determined to be ill-conditioned or if one or more of the angles is below a certain threshold 24. A method according to any of clauses 21 to 23, wherein the reconstruction optimization step comprises:
determining one or more sets of correlated geometric parameters, and
determining as variable geometric parameters, the correlated geometric parameter of each set which is deemed to have the greatest relative importance within the set.

25. A method according to any preceding clause, wherein the target comprises at least two sub-targets, each having a different imposed overlay bias.

26. A method according to any preceding clause, wherein there are a plurality of variable geometric parameters, and wherein the minimization step comprises simultaneously reconstructing values for each of these variable geometric parameters.

27. A method according to clause 26, wherein the number of variable geometric parameters is greater than three.

28. A method according to clause 26, wherein the number of variable geometric parameters is greater than six.

29. A method according to any preceding clause, wherein the simulation data is obtained from a point spread function model.

30. A method according to any preceding clause, comprising performing the measurement and capturing the at least one corresponding pair of non-zeroth diffraction orders to obtain the measurement data and performing the simulation to obtain the simulation data.

31. A method according to any preceding clause, wherein the measurement data relates to measurement of the target with measurement radiation having a plurality of different measurement radiation characteristics.

32. A method according to any preceding clause, wherein the target is no larger than 10 μm in either dimension in the substrate plane.

33. A metrology apparatus comprising a processor operable to at least:
obtain measurement data relating to a measurement of a target formed in at least two layers on a substrate by a lithographic process, the measurement data being derived from at least one corresponding pair of non-zeroth diffraction orders;
obtain simulation data relating to simulation of a measurement of the target as defined in terms of geometric parameters of the target, the geometric parameters comprising one or more variable geometric parameters; and
minimize the difference between the measurement data and simulation data, so as to directly reconstruct values for the one or more variable geometric parameters.

34. A metrology apparatus according to clause 33, comprising a detector in an image plane of the metrology apparatus and being operable to perform dark-field measurements, wherein the at least one corresponding pair of non-zeroth diffraction orders is detected by the detector in the image plane to obtain the measurement data.

35. A metrology apparatus according to clause 34, being operable to minimize the difference between the measurement data and simulation in terms of an intensity metric of the detected non-zeroth diffraction orders.

36. A metrology apparatus according to clause 35, wherein the measurement data and simulation data each comprises a plurality of intensity values, one for each combination of non-zeroth diffraction order, measurement radiation characteristic, and/or imposed target bias comprised in the target, the processor being operable to derive the intensity metric from the intensity values.

37. A metrology apparatus according to clause 35 or clause 36, wherein the intensity metric comprises scaled image intensity asymmetry, scaled image intensity asymmetry comprising an intensity difference between corresponding pairs of non-zeroth diffraction orders scaled by their average intensity.

38. A metrology apparatus according to clause 35 or clause 36, wherein the intensity metric comprises stack sensitivity, wherein stack sensitivity is the ratio of an overlay proportionality constant to an average of intensities of regions of interest within the measurement image.

39. A metrology apparatus according to clause 35 or clause 36, wherein the intensity metric comprises average intensity, average intensity being an average of intensities of regions of interest within the measurement image.

40. A metrology apparatus according to clause 33, comprising a detector in a pupil plane of the metrology apparatus and being operable to perform pupil-plane measurements, wherein the at least one corresponding pair of non-zeroth diffraction orders is detected by the detector in the pupil plane to obtain the measurement data.

41. A metrology apparatus according to any of clauses 33 to 40, wherein the one or more variable geometric parameters comprise at least one layer height of a layer comprised in the target.

42. A metrology apparatus according to clause 41, wherein the one or more variable geometric parameters comprise a plurality of layer heights of different layers comprised in the target, and wherein the processor is operable to simultaneously reconstruct values for the plurality of layer heights.

43. A metrology apparatus according to clause 41 or 42, wherein the processor is further operable to:
calculate a spectral sequence describing a variation of an intensity parameter with wavelength of measurement radiation for the target with the at least one layer height as determined in the minimization; and optimize the measurement radiation based on the spectral sequence.

44. A metrology apparatus according to any of clauses 33 to 43, wherein the one or more variable geometric parameters comprise overlay error absent of the effects of geometric asymmetry in at least one of the structures comprised in the target.

45. A metrology apparatus according to any of clauses 33 to 44, wherein the one or more variable geometric parameters comprise one or more geometric asymmetry parameters of at least one of the structures comprised in the target.

46. A metrology apparatus according to any of clauses 33 to 39, wherein the one or more variable geometric parameters comprise:
one or more layer heights of layers comprised in the target; and
one or more other variable geometric parameters which may comprise one or more selected from: overlay error absent of the effects of geometric asymmetry in at least one of the structures comprised in the target and/or one or more geometric asymmetry parameters,
wherein the processor is operable to perform the minimization in two stages, a first stage for reconstructing values for the one or more layer heights and a second stage for reconstructing values for the one or more other variable geometric parameters, the one or more layer heights determined in the first stage being fed forward as one or more fixed layer height parameters in the second stage.

47. A metrology apparatus according to clause 46, wherein the intensity metric comprises stack sensitivity in the first stage, wherein stack sensitivity is the ratio of an overlay proportionality constant to an average of the intensities of regions of interest within the measurement image; and wherein the intensity metric comprises scaled image intensity asymmetry in the second stage, the scaled image intensity asymmetry comprising an intensity difference between corresponding pairs of non-zeroth diffraction orders scaled by their average intensity.

48. A metrology apparatus according to clause 46 or 47, wherein the processor is operable in the first stage to predict a stack height variation map which describes the variation of the layer heights across the substrate, and in the second stage to use the stack height variation map to determine the one or more fixed layer height parameters.

49. A metrology apparatus according to any of clauses 46 to 48, wherein the processor is further operable to:
calculate a spectral sequence describing a variation of an intensity parameter with wavelength of measurement radiation for the target with the at least one layer height as determined in the minimization; and
optimize the measurement radiation based on the spectral sequence.

50. A metrology apparatus according to any of clauses 45 to 49, wherein the one or more geometric asymmetry parameters comprise one or more selected from: floor tilt, top tilt, side wall angle, and/or critical dimension.

51. A metrology apparatus according to any of clauses 33 to 50, wherein the processor is operable to devise an objective function for minimizing the difference between the measurement data and the simulation data.

52. A metrology apparatus according to clause 51, wherein the objective function comprises a term which accounts for detector noise.

53. A metrology apparatus according to clause 51 or clause 52, wherein the processor is operable to determine which one or more of the geometric parameters should be included in the variable geometric parameters.

54. A metrology apparatus according to clause 53, wherein, with respect to each geometric parameter, the processor is further operable to:
determine a derivative matrix of the objective function; and
determine which one or more of the geometric parameters should be included in the variable geometric parameters based on the conditionality of the derivative matrix and angles of different vector(s) combinations within the derivative matrix.

55. A metrology apparatus according to clause 54, wherein the processor is further operable to not select a geometric parameter to be a variable geometric parameter if the corresponding derivative matrix is determined to be ill-conditioned or if one or more of the angles is below a certain threshold 56. A metrology apparatus according to clause 53, 54 or 55, wherein the processor is further operable to:
determine one or more sets of correlated geometric parameters, and
determine as variable geometric parameters, the correlated geometric parameter of each set which is deemed to have the greatest relative importance within the set.

57. A metrology apparatus according to any of clauses 33 to 56, wherein there are a plurality of variable geometric parameters, and wherein the processor is further operable to simultaneously reconstruct values for each of these variable geometric parameters.

58. A metrology apparatus according to clause 57, wherein the number of variable geometric parameters is greater than three.

59. A metrology apparatus according to clause 57, wherein the number of variable geometric parameters is greater than six.

60. A metrology apparatus according to any of clauses 33 to 59, wherein the simulation data is obtained from a point spread function model.

61. A metrology apparatus according to any of clauses 33 to 60, comprising a radiation source for providing measurement radiation to measure the target and obtain the measurement data.

62. A metrology apparatus according to clause 61, wherein the radiation source is operable to provide measurement radiation with a plurality of different measurement radiation characteristics, such that the measurement data relates to measurement of the target with measurement radiation with the plurality of different measurement radiation characteristics.

63. A metrology apparatus according to any of clauses 33 to 62, being operable to measure a target which is no larger than 10 μm in either dimension in the substrate plane.

64. A computer program comprising program instructions operable to perform the method of any of clauses 1 to 32 when run on a suitable apparatus.

65. A non-transient computer program carrier comprising the computer program of clause 64.

Although specific reference may have been made above to the use of embodiments of the invention in the context of optical lithography, it will be appreciated that embodiments of the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

The foregoing description of the specific embodiments reveals the general nature of embodiments of the invention such that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description by example, and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:
1. A metrology method comprising:
  obtaining measurement data relating to a measurement of a target formed in at least two layers on a substrate by a lithographic process, the measurement data being derived from a corresponding pair of non-zeroth diffraction orders;
  obtaining simulation data relating to a simulation of a measurement of the target as defined in terms of geometric parameters of the target, the geometric parameters comprising a variable geometric parameter; and
  minimizing a difference between the measurement data and the simulation data, so as to directly reconstruct a value for the variable geometric parameter.
2. The method as claimed in claim 1, wherein the measurement data relates to a measurement of the target derived from a dark-field measurement and wherein the corresponding pair of non-zeroth diffraction orders is detected in an image plane.
3. The method as claimed in claim 1, wherein the minimizing is performed to minimize the difference between the measurement data and the simulation data in terms of an intensity metric of the detected corresponding pair of non-zeroth diffraction orders.
4. The method as claimed in claim 3, wherein the measurement data and the simulation data each comprises a plurality of intensity values, one for each combination of non-zeroth diffraction order, measurement radiation characteristic, and/or imposed target bias comprised in the target, and the intensity metric is derived from the plurality of intensity values.
5. The method as claimed in claim 3, wherein the intensity metric comprises a scaled image intensity asymmetry metric, the scaled image intensity asymmetry metric comprising an intensity difference between corresponding pairs of non-zeroth diffraction orders scaled by their average intensity.
6. The method as claimed in claim 3, wherein the intensity metric comprises a stack sensitivity metric, wherein the stack sensitivity metric is a ratio of an overlay proportionality constant to an average of intensities of regions of interest within a measurement image.
7. The method as claimed in claim 3, wherein the intensity metric comprises an average intensity metric, the average intensity metric being an average of intensities of regions of interest within a measurement image.
8. The method as claimed in claim 1, wherein the measurement data relates to a measurement of the target derived from a measurement with respect to a pupil plane and wherein the corresponding pair of non-zeroth diffraction orders is detected in the pupil plane.
9. The method as claimed in claim 1, wherein the variable geometric parameter comprises a layer height of a layer comprised in the target.
10. The method as claimed in claim 9, wherein the variable geometric parameter comprises a layer height of each layer of a plurality of different layers comprised in the target, and wherein the minimizing comprises simultaneously reconstructing values for the layer heights of the plurality of different layers.
11. The method as claimed in claim 9, further comprising:
  calculating a spectral sequence describing a variation of an intensity parameter with wavelength of measurement radiation, for the target with the layer height as determined in the minimizing; and
  optimizing the measurement radiation based on the spectral sequence.
12. The method as claimed in claim 1, wherein the variable geometric parameter comprises a geometric asymmetry parameter of a structure comprised in the target.
13. The method as claimed in claim 12, wherein the geometric asymmetry parameter comprises one or more selected from: floor tilt, top tilt, side wall angle, and/or critical dimension.
14. The method as claimed in claim 1, wherein the variable geometric parameter comprises:
  a layer height of a layer comprised in the target; and
  another variable geometric parameter,
  wherein the minimizing is performed in two stages, a first stage for reconstructing a value for the layer height and a second stage for reconstructing a value for the other variable geometric parameter, the layer height determined in the first stage being fed forward as a fixed layer height parameter in the second stage.
15. The method as claimed in claim 14, wherein the minimizing is performed to minimize the difference between the measurement data and the simulation data in terms of an intensity metric,
  wherein the intensity metric comprises a stack sensitivity metric in the first stage, wherein the stack sensitivity metric is a ratio of an overlay proportionality constant to an average of intensities of regions of interest within a measurement image, and
  wherein the intensity metric comprises a scaled image intensity asymmetry metric in the second stage, the scaled image intensity asymmetry metric comprising an intensity difference between corresponding pairs of non-zeroth diffraction orders scaled by an average intensity of the corresponding pairs of non-zeroth diffraction orders.

16. The method as claimed in claim 14, wherein the first stage is used to predict a stack height variation map which describes variation of the layer height across the substrate, the stack height variation map being used to determine the fixed layer height parameter in the second stage.

17. The method as claimed in claim 14, further comprising:
calculating a spectral sequence describing a variation of an intensity parameter with wavelength of measurement radiation, for the target with the layer height as determined in the minimizing; and
optimizing the measurement radiation based on the spectral sequence.

18. The method as claimed in claim 1, wherein the minimizing comprises devising an objective function for minimizing the difference between the measurement data and the simulation data.

19. A metrology apparatus comprising a processor configured to at least:
obtain measurement data relating to a measurement of a target formed in at least two layers on a substrate by a lithographic process, the measurement data being derived from a corresponding pair of non-zeroth diffraction orders;
obtain simulation data relating to a simulation of a measurement of the target as defined in terms of geometric parameters of the target, the geometric parameters comprising a variable geometric parameter; and
minimize a difference between the measurement data and the simulation data, so as to directly reconstruct a value for the variable geometric parameter.

20. A non-transitory computer-readable medium comprising instructions therein, the instructions, upon execution by a computer system, configured to cause the computer system to at least:
obtain measurement data relating to a measurement of a target formed in at least two layers on a substrate by a lithographic process, the measurement data being derived from a corresponding pair of non-zeroth diffraction orders;
obtain simulation data relating to a simulation of a measurement of the target as defined in terms of geometric parameters of the target, the geometric parameters comprising a variable geometric parameter; and
minimize a difference between the measurement data and the simulation data, so as to directly reconstruct a value for the variable geometric parameter.

* * * * *